(12) United States Patent
Henry et al.

(10) Patent No.: US 6,536,270 B1
(45) Date of Patent: Mar. 25, 2003

(54) SCANNER WITH INTERIOR GAUGING HEAD AND DUST BELT

(75) Inventors: Lee L. Henry, San Jose, CA (US); Steven Nelson, Oroville, CA (US)

(73) Assignee: Voith Paper Automation, Inc., Los Gatos, CA (US)

(*) Notice: Subject to any disclaimer, the term of this patent is extended or adjusted under 35 U.S.C. 154(b) by 0 days.

(21) Appl. No.: 09/885,941

(22) Filed: Jun. 20, 2001

Related U.S. Application Data

(63) Continuation-in-part of application No. 09/487,058, filed on Jan. 19, 2000, now Pat. No. 6,253,604.

(51) Int. Cl.[7] ................................................. G01L 5/04
(52) U.S. Cl. ........................ 73/159; 73/159; 73/73; 162/198; 162/263; 250/339.1
(58) Field of Search ............................ 73/198, 73, 159; 162/198, 263; 250/339.1; 356/640

(56) References Cited

U.S. PATENT DOCUMENTS

| | | | | |
|---|---|---|---|---|
| 3,621,259 A | * | 11/1971 | Boissevain et al. | 250/360.1 |
| 4,791,353 A | * | 12/1988 | Typpo | 324/667 |
| 5,164,048 A | | 11/1992 | Bossen et al. | |
| 5,165,277 A | * | 11/1992 | Bossen et al. | 73/159 |
| 5,298,122 A | * | 3/1994 | Munch et al. | 162/259 |
| 5,343,296 A | | 8/1994 | Hellstrom | |
| 5,658,432 A | * | 8/1997 | Heaven et al. | 162/198 |
| 5,773,714 A | * | 6/1998 | Shead | 73/105 |
| 5,928,475 A | * | 7/1999 | Chase et al. | 162/198 |
| 6,080,278 A | * | 6/2000 | Heaven et al. | 162/198 |
| 6,168,687 B1 | * | 2/2001 | Hu et al. | 162/198 |

FOREIGN PATENT DOCUMENTS

| | | |
|---|---|---|
| EP | 0 868 570 A | 10/1998 |
| EP | 1 126 274 A2 | 8/2001 |
| GB | 1 420 854 A | 1/1976 |

\* cited by examiner

*Primary Examiner*—Daniel S. Larkin
*Assistant Examiner*—André K. Jackson
(74) *Attorney, Agent, or Firm*—Coudert Brothers LLP

(57) ABSTRACT

A scanner for moving sheet materials such as a paper making machine provides the gauging heads which measure parameters such as basis weight and moisture entirely inside an enclosed tubular beam. Each gauging head is driven in a cross direction perpendicular to the moving sheet direction and includes a seal belt for dust and dirt protection by covering a slot in the beam, except where the gauging is located.

17 Claims, 11 Drawing Sheets

SCANNER WITH INTERIOR GAUGING HEAD AND DUST BELT

RELATED APPLICATIONS

The present application is a continuation in part of No. 09/487,058 filed Jan. 19, 2000, now U.S. Pat. No. 6,253,604.

INTRODUCTION

The present invention is directed to a scanner for measuring at least one parameter of a sheet material such as the basis weight or moisture content of paper and, more specifically, to a scanner which has a dust belt which protects a gauging head which is contained entirely within a tubular beam suspended across the sheet material.

BACKGROUND OF THE INVENTION

For the measurement of the properties or parameters of a moving paper sheet a pair of gauging heads are used which scan the sheet of material in a cross direction (CD) with material moving in a machine direction (MD). The gauging heads themselves are mounted on a pair of spaced upper and lower beams as more fully disclosed or shown in the above pending application. Normally, the gauging heads are external to the beams which are in a cross direction across a moving paper sheet and since the gauging head operates in an extremely hot or moist environment, cooling water or cooled air must be supplied by a separate unit in the beam to the gauging heads. Also, the upper and lower gauging heads must move in perfect synchronism to reduce measurement errors.

OBJECT AND SUMMARY OF INVENTION

It is a general object of the present invention to provide an improved scanner for measuring at least one parameter of a sheet of moving material.

In accordance with the above object, there is provided a scanner for measuring at least one parameter of a sheet of material moving in a machine direction(MD) including gauging head means mounted for cross direction (CD) movement across the sheet, and perpendicular to the MD, from one edge of the sheet to the other comprising at least one tubular beam suspended over or under the sheet in the CD from one the edge to the other, the beam having a continuous slot in the CD in proximity to such sheet to allow the gauging means to measure the parameter. Guide means are inside the tubular beam on which the gauging head means is interiorly mounted for CD movement within the tubular beam, such gauging head means having a face exposed through the slot to the sheet without physical interference for measuring a the parameter of the sheets. Seal belt means are substantially contained within the tubular beam and connected to the gauging head for sealing the length of the slot in the CD to protect the interior of the beam and the gauging head from ambient dust, dirt, and air, the sealing belt means including an opening at the gauging head to allow direct communication, without interference, between the gauging head face and the moving sheets. Means are provided for driving the gauging head in the CD.

DETAILED DESCRIPTION OF THE PREFERRED EMBODIMENTS

Figure 1:
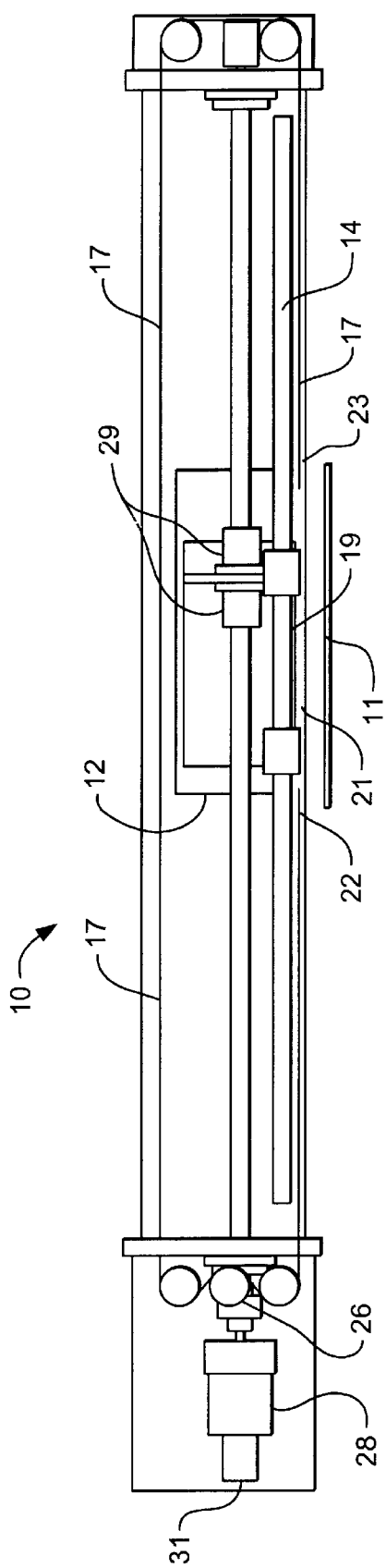
FIG. 1 is a side view of a scanner incorporating the invention which is partially cut-away.
Figure 2:
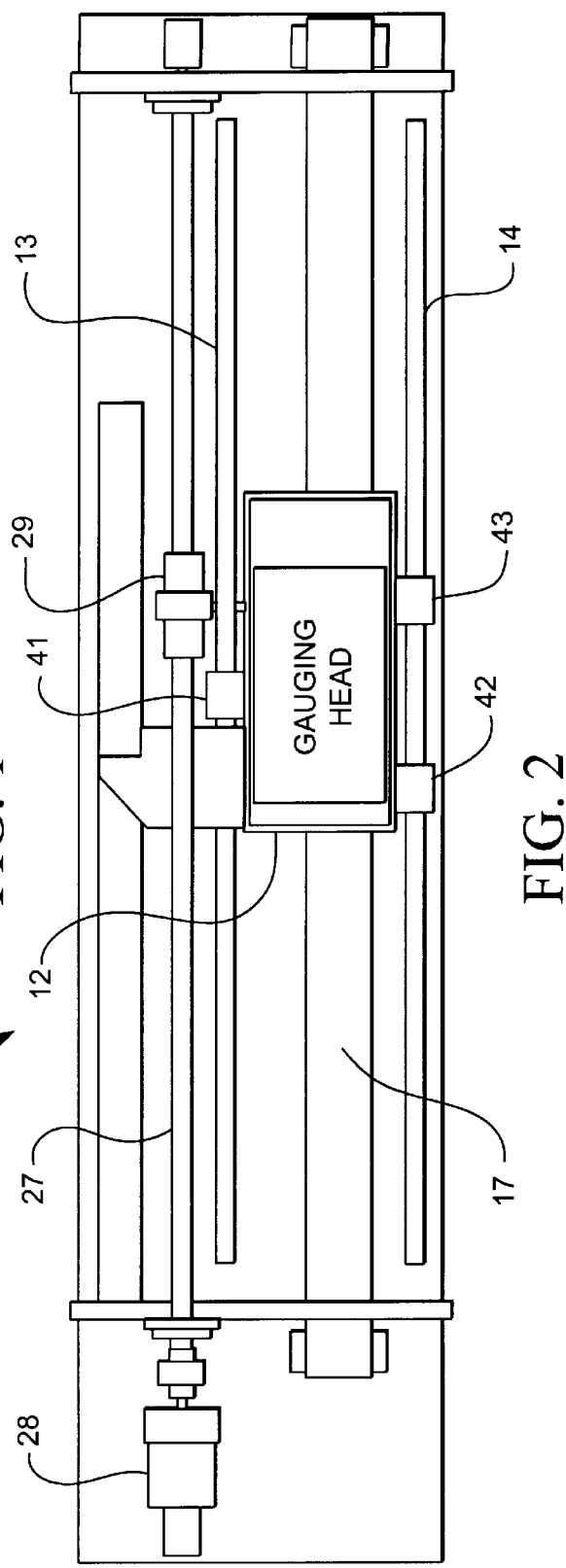
FIG. 2 is a cut-away top view of FIG. 1.
Figure 4:
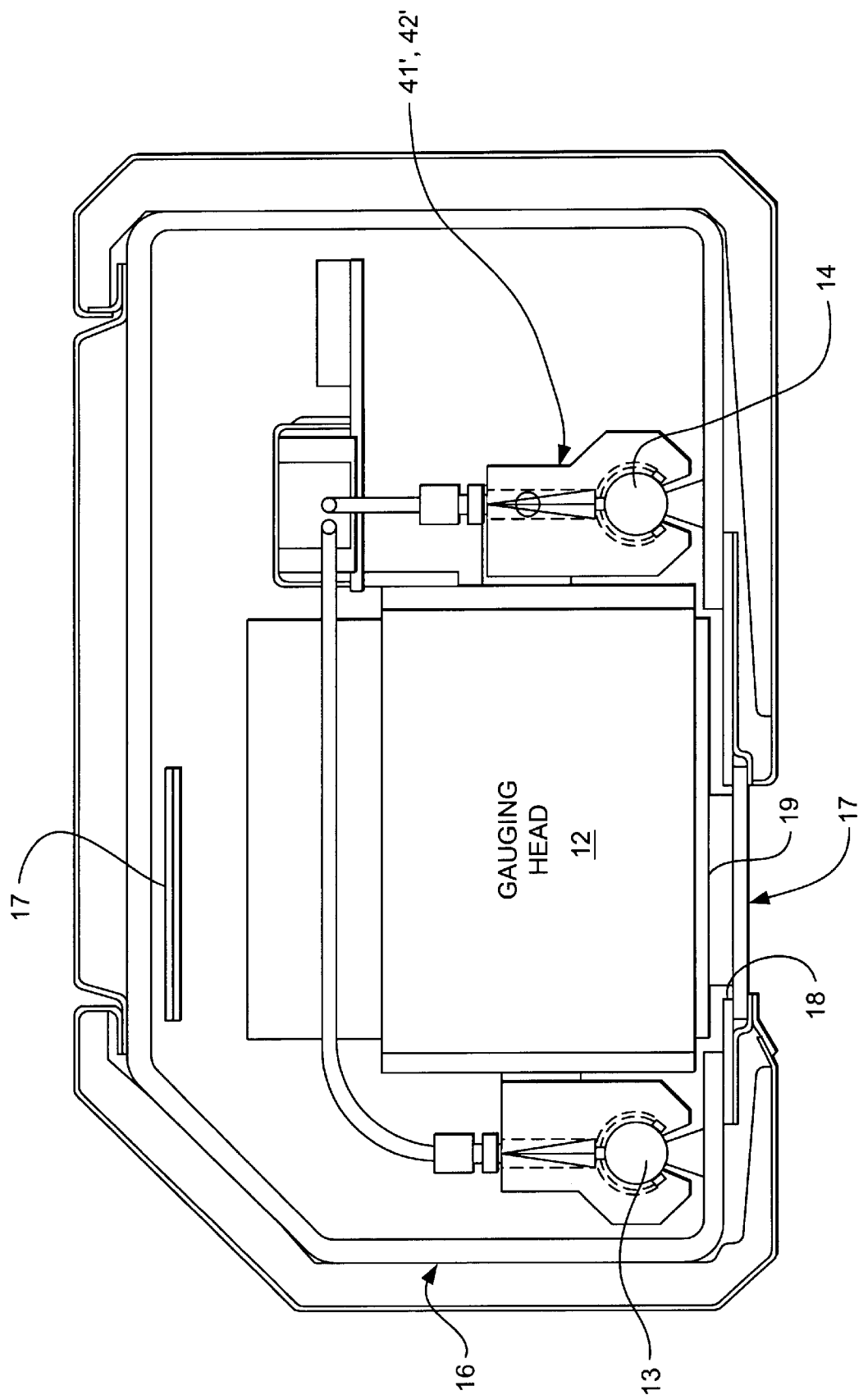
FIG. 4 is a cross-sectional view of FIGS. 1 or 2 but illustrating a modification of the invention.

FIG. 1 illustrates a scanner 10 which is suspended in a cross-direction (CD) across a moving sheet material 11 such as paper which is moving in a machine direction (MD) which is perpendicular to the cross-direction in the same plane. Referring also to FIG. 2, a gauging head 12 is mounted for a cross-direction movement across the sheet and is mounted for slideable movement on a pair of rails 13 and 14. Gauging head 12 is completely contained within the interior of a tubular beam 16, as illustrated in FIG. 4, and is suspended across the moving paper sheet 11. Thus the gauging head 12 moves from one edge of the sheet to the other within the beam. It is protected from the severe heat and moisture environment which is normal in the paper making industry by a seal belt 17 which covers a continuous slot 18 in the bottom of the tubular beam 16. Gauging head 12 has a face 19 exposed through an opening 21 (FIG. 1) in the belt 17 so that the infrared red light or radiation may pass through the opening and through the sheet to measure, for example, moisture and/or a basis weight. Normally, another gauging head on the other side of the sheet would receive any transmitted radiation or infrared light.

Referring back to FIG. 1, the seal belt 17 provides the opening 21 by being fixed at the end points 22 and 23 of the gauging head 12. The foregoing is more fully discussed in the above U.S. Pat No. 6,253,604. As discussed in that patent, and more fully illustrated in FIG. 12 of this application, the gauging head 12 which normally moves with the sealing belt 17 may also be driven by the motor 28 driving the pulley system 25. Alternatively, as illustrated in FIG. 1 and FIG. 2, the seal belt 17 may be freely moveable. See the pulley system at 26 which includes a tensioning pulley. Instead the gauging head may be driven by a shaft 27 journaled in the beam in a cross-direction driven by a motor 28 which drives, via a pair of dual pre-loaded ball screw nuts 29, the gauging head since the ball screw nuts 29 are attached to gauging head 12. At the end of the motor 28 there may be placed a rotary encoder 31 to determine the location of the gauging heads within a scan.

Figure 3:
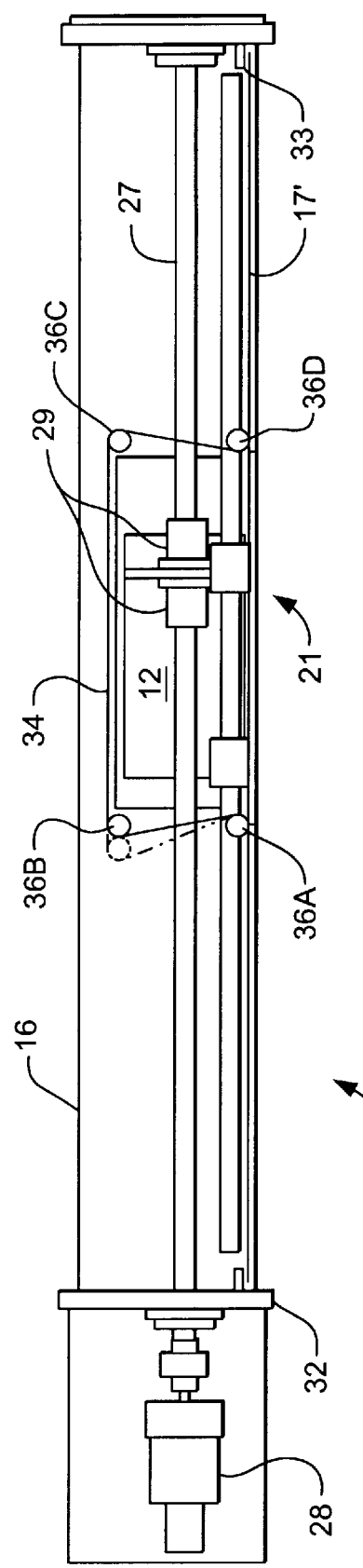
FIG. 3 is a cross-sectional elevation view of a scanner similar to FIG. 1 but which illustrates a different embodiment.

FIG. 3 is an alternative to FIG. 1 where the same type of drive; that is the shaft 27 with the dual pre-loaded screw nuts 29 is utilized for driving the gauging head 12. However, here the seal belt 17' is actually clamped at the ends of the beam 32 and 33. In order to provide an opening 21 the belt is looped in a loop 34 via the pulleys 36a–36d over the rear of the gauging head 12 in the interior of the beam 16. This effectively provides a suitable opening 21 while still sealing the remainder of the slot in the beam 16. Roller 36b is a seal belt tensioning roller as indicated by the dashed outline. It is spring loaded to maintain tension in the belt; in other words, it is flexibly biased.

Referring now to FIG. 4, as well as FIG. 2, the gauging head is normally slideably mounted on the bearings 41, 42 and 43 which slide on the rails 13 and 14. However, the modification of FIG. 4 shows rather than normal bearings such as ball bearings, that magnetic levitation may be used for interacting with the rails. Thus, the bearing blocks 41' and 42' are specially fitted with electromagnetics which are 120 electrical degrees apart in order to provide a magnetic levitation system.

Figure 5:
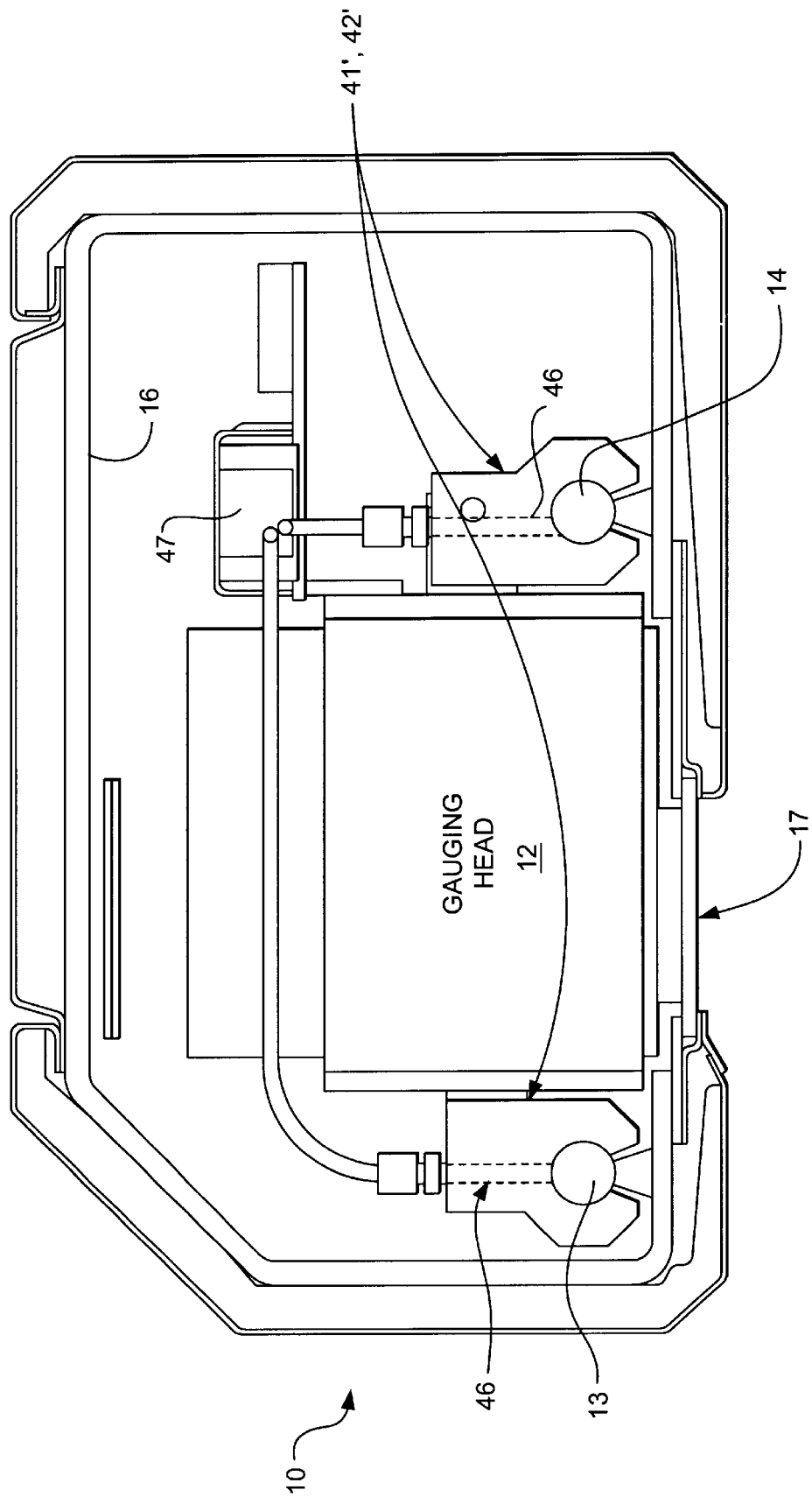
FIG. 5 is cross-sectional view similar to FIG. 4 illustrating another embodiment.

FIG. 5 illustrates another type of bearing block in which bearing blocks 41' and 42' include specialty machined air outlets 46 to provide air bearings. These are fed from an air supply 47 mounted within the beam 16.

Figure 7:
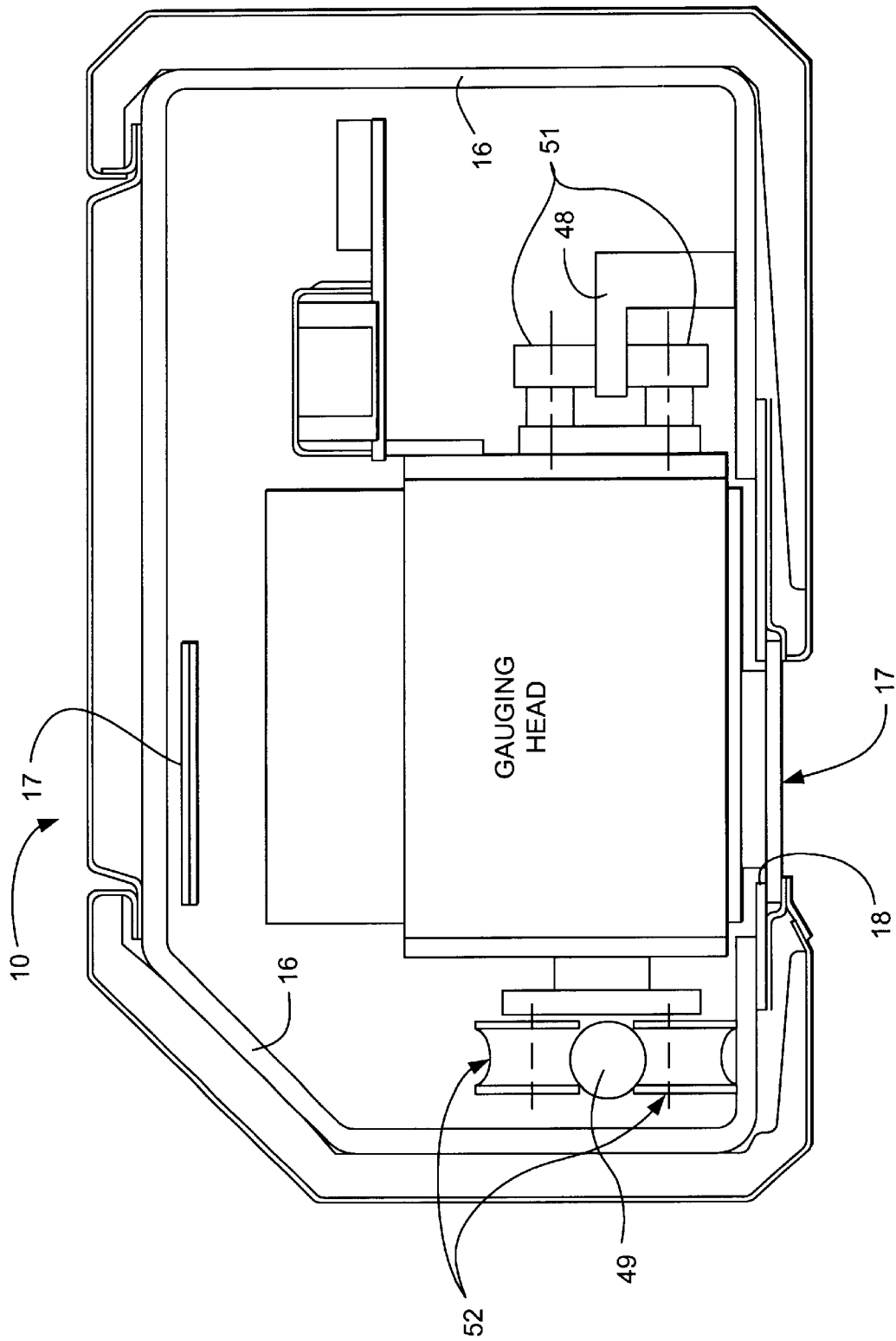
FIG. 7 is a cross-sectional view similar to FIG. 4 but illustrating another embodiment.

FIG. 7 illustrates yet another bearing system where, rather than the precision linear rails 13 and 14 illustrated for example in FIG. 2, one rail 48 may be flat and L-shaped and mounted to the interior of the beam 16 and the other rail 49 cantilevered from the side of beam 16. Then a pair of opposing flat rollers 51 are used to ride on the flat rail 48 and a pair of concave rollers 52 ride on the cantilevered rail 49. This rail also provides positioning to keep the movement of the gauging heads centered along the slot.

Figure 6:
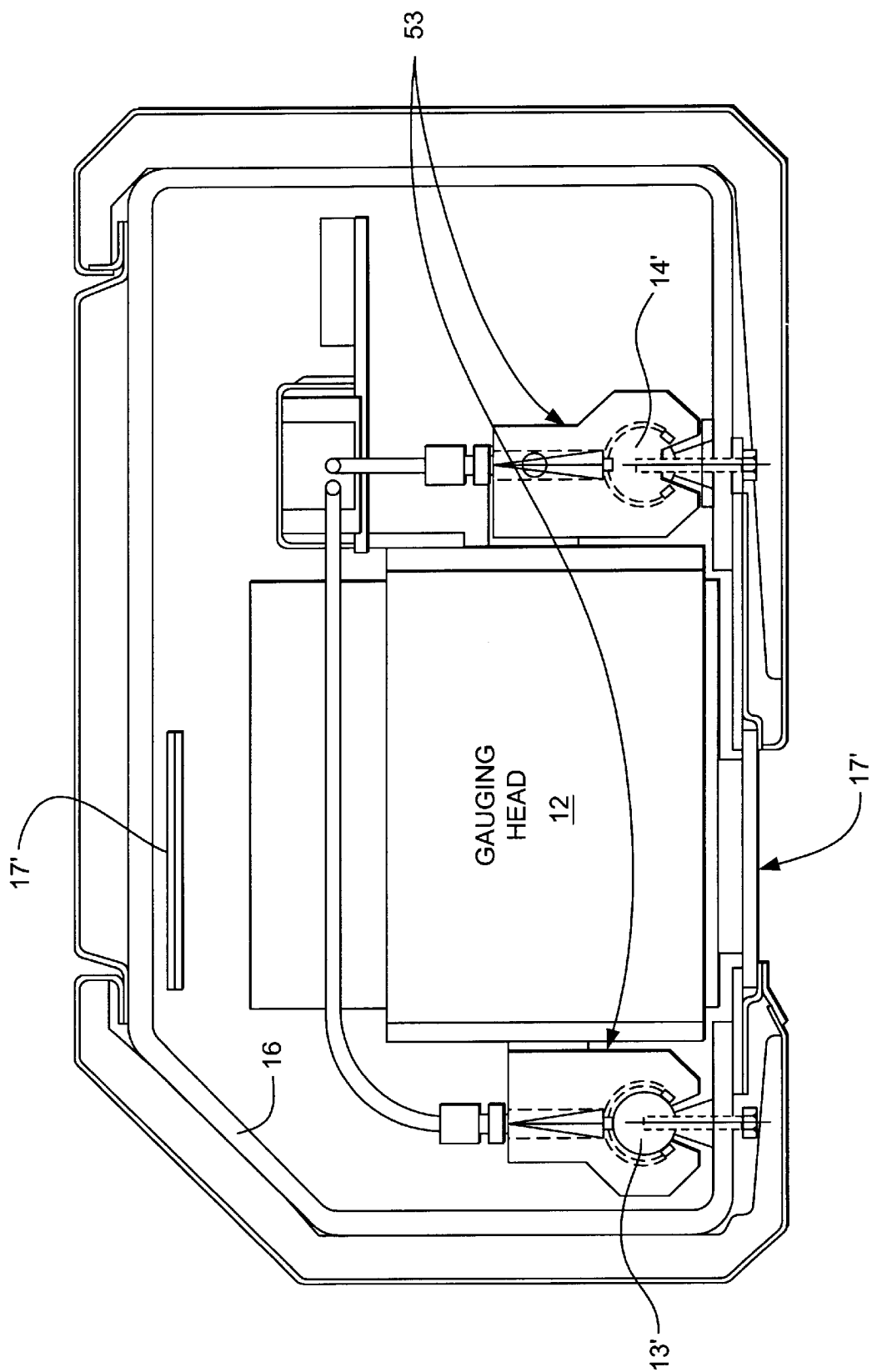
FIG. 6 is a cross-sectional view similar to FIG. 5 but illustrating another embodiment of the invention.

Referring now to FIG. 6, this is a cross-sectional view similar to FIG. 4 where however the belt 17' forms a freely moveable loop. Here the gauging head 12 still rides on tubular rails 13' and 14' which are electrically isolated from the beam 16 to allow them to be electrically charged to achieve linear motion. Such linear motion is achieved by the pair of bearing blocks 53 which have specially fitted electromagnetics 120 electrical degrees apart. Thus in a manner similar to that used for magnetic prime motion in the railroad field, the gauging head 12 may be scanned. In other words, a linear motor is provided.

Figure 8:
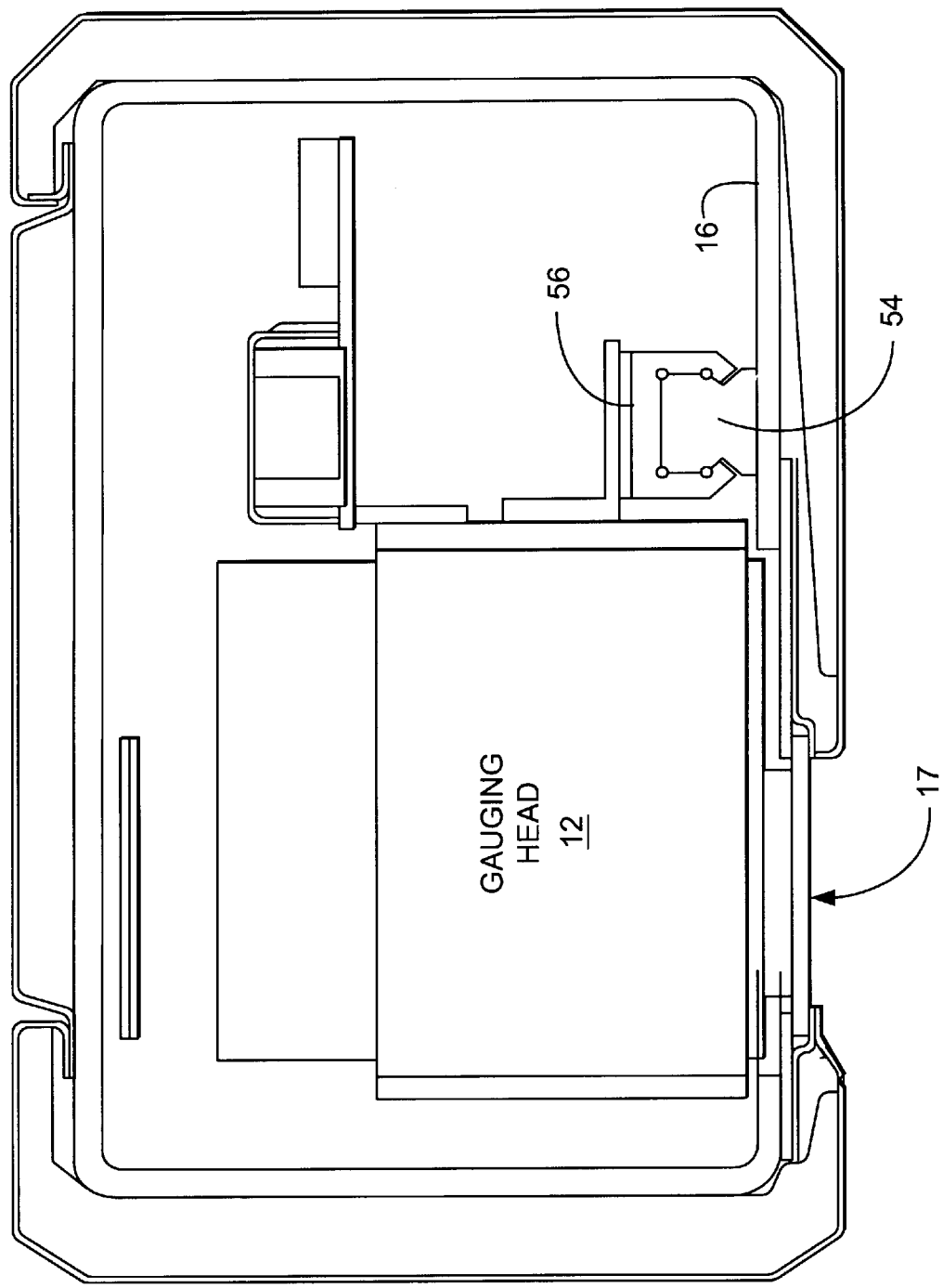
FIG. 8 is a cross-sectional view similar to FIG. 4 but illustrating another embodiment of the invention.

FIG. 8 shows yet another suspension system for the gauging head 12 where a faceted rail 54 which is fastened to the bottom of 16 allows the gauging head 12 to be cantilevered by use of a high moment capacity linear bearing 56 attached to the side of the gauging head 12 interacting with the faceted rail 54 to allow it to slide. Seal belt 17 would normally be a driven belt.

Figure 9:
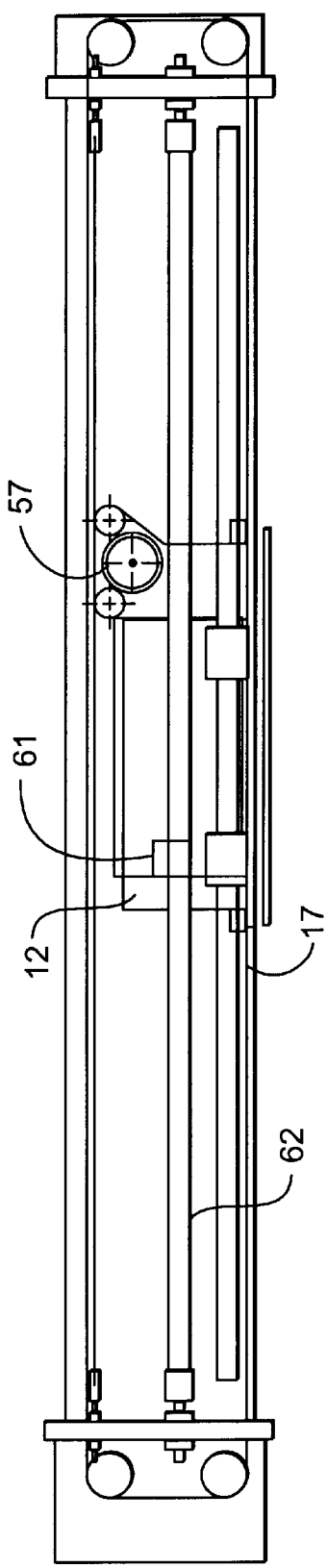
FIG. 9 is a cross-sectional elevational view similar to FIG. 1 but illustrating another embodiment of the invention.
Figure 10:
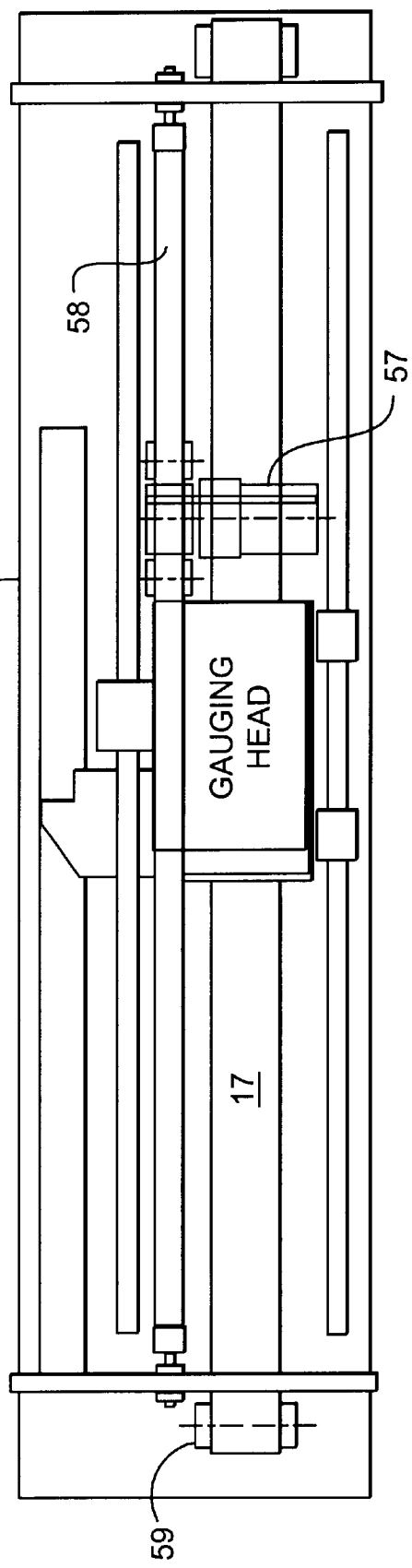
FIG. 10 is a top view of FIG. 9 partially cut away.

Now referring to FIGS. 9 and 10, here the sealing belt 17 is freely moveable but the gauging head 12 is scanned in the cross direction by an integrally mounted drive motor 57 which meshes with a linear belt 58 fixed in a cross direction inset in the beam 16. A tensioning device is provided at the end of belt 58. The belt may be of a timing belt type with grooves or a roller chain. For the position of the gauging head 12 either a rotary decoder may be used at the end of the freely moveable seal belt 17 indicated at 59 or a sonic linear transducer 61 may be mounted on a tensioned stainless steel band 62 to provide periodic pulses as the gauging head 12 moves along the band 62.

Figure 11:
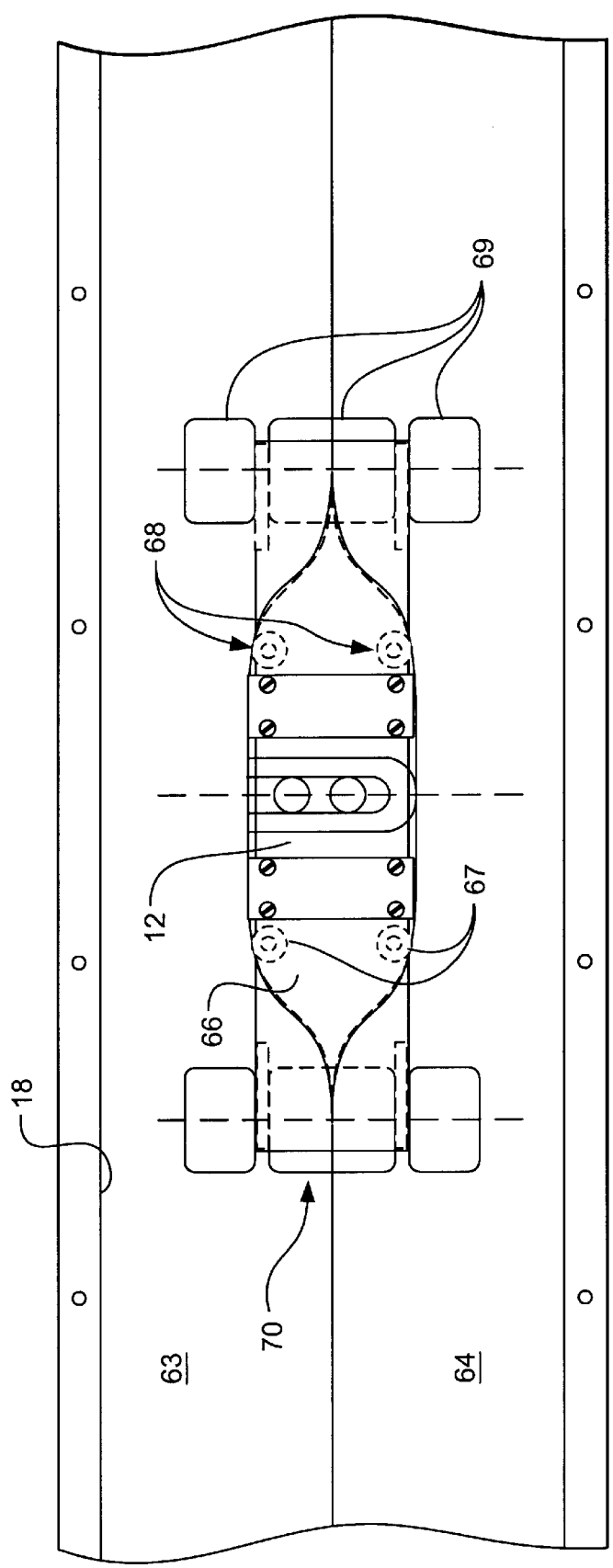
FIG. 11 is a bottom view of a modification of FIG. 3.

FIG. 11 illustrates an alternative embodiment of the sealing belt 17 where it is still placed in a slot 18, but it is divided into flexible strips 63 and 64 which extend the length of the slot 18. The sensor windows of gauging head 12 are provided at opening 66 by use of two pairs of spaced rollers 67 and 68 mounted to the gauging head 12 which spread the strips 63 and 64 apart as the gauging head scans across the moving paper sheet. Appropriate flattening rollers 69 and 70 are attached to the gauging head to again reclose the seal belt.

Figure 12:
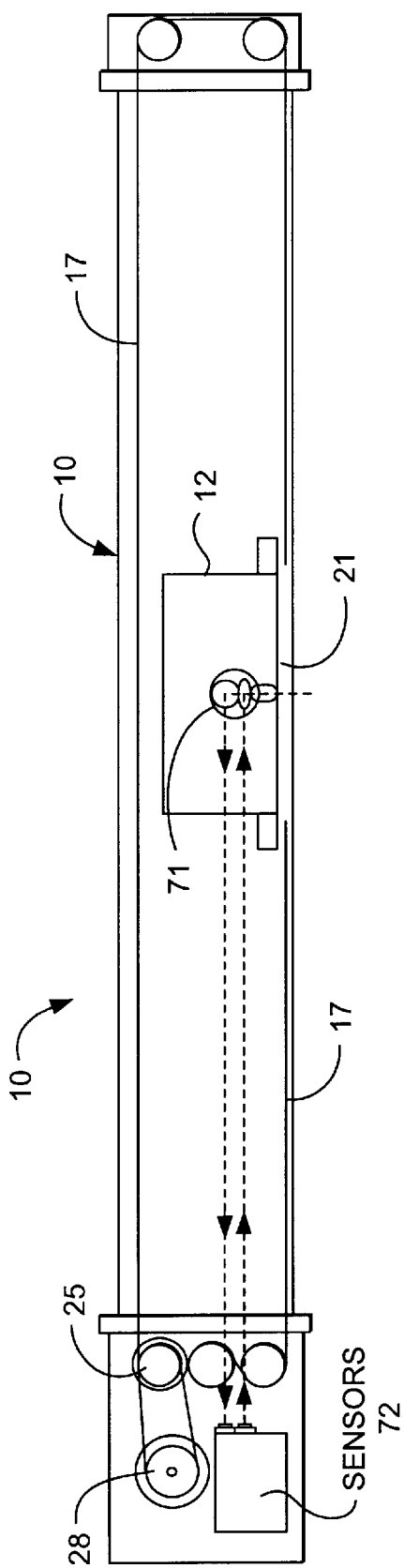
FIG. 12 is a side elevational view partially cut away of a scanner embodying the present invention.
Figure 13:
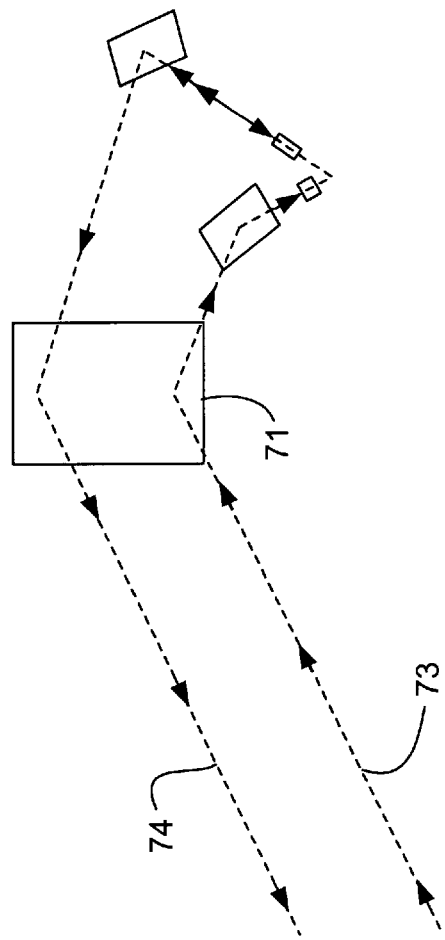
FIG. 13 is a diagram useful in understanding the operation of FIG. 12.

Referring now to FIG. 12 for transmitting infrared information from the gauging head 12, which would normally contain moisture information, rather than using a flexible continuous cable a mirror 71 may be utilized. See also FIG. 13. Here the infrared sensor box 72 at the receiver end of the scanner beam transmits an infrared beam 73 which is absorbed by the moving paper sheet and then the amount of attenuation shown by the reflected beam 74. As discussed above, the gauging head 12 is driven by a combined driving/seal belt 17, and driven by motor 28 in the pulley system 25.

Figure 14:
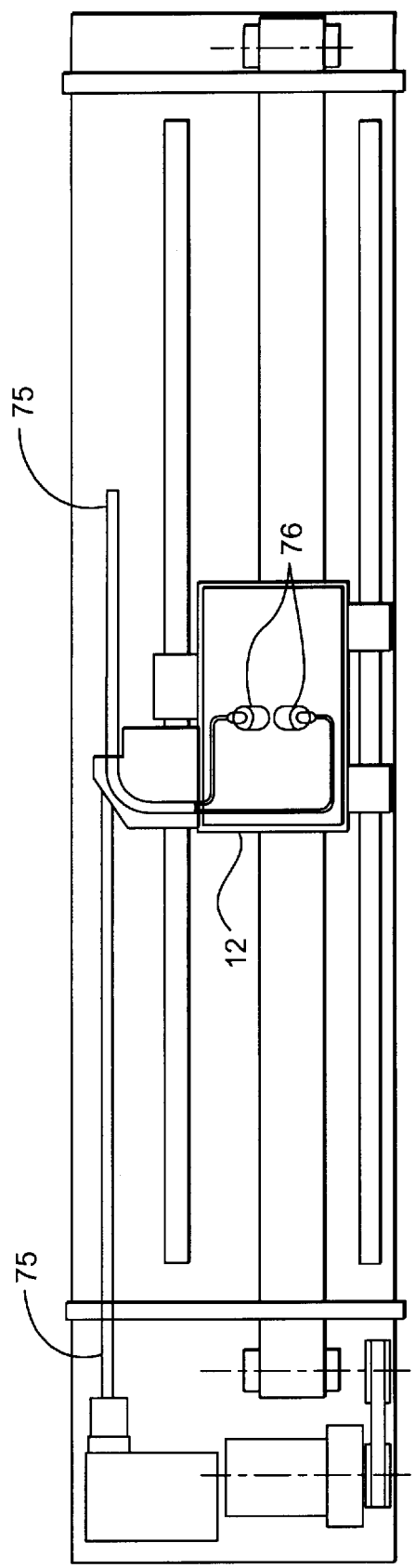
FIG. 14 is a top view of a scanner showing another embodiment of the invention which is partially cut away.

FIG. 14 shows another information transmission technique for infrared information where rather than transmissions into the air, a fiber optic cable 75 is flexibly mounted to the gauging head 12 and connected to the gauging head optics 76.

In summary, a scanner having an interior gauging head has been provided.

What is claimed is:

1. A scanner for measuring at least one parameter of a sheet of material moving in a machine direction(MD) including gauging head means mounted for cross direction (CD) movement across the sheet, and perpendicular to the MD, from one edge of the sheet to the other comprising:

at least one tubular beam suspended over or under the sheet in the CD from one the edge to the other, the beam having a continuous slot in the CD in proximity to such sheet to allow the gauging means to measure the parameter;

guide means inside the tubular beam on which the gauging head means is interiorly mounted for CD movement within the tubular beam, such gauging head means having a face exposed through the slot to the sheet without physical interference for measuring a parameter of the sheet;

seal belt means substantially contained within the tubular beam and forming a freely movable loop within said beam and connected to the gauging head for sealing the length of the slot in the CD to protect the interior of the beam and the gauging head from ambient dust, dirt, and air, the sealing belt means including an opening at the gauging head to allow direct communication, without interference, between the gauging head face and the moving sheet;

and means for driving the gauging head means in the CD.

2. A scanner as in claim 1 where the driving means includes a driven rotary ball screw shaft journalled in the beam in the CD and the gauging head includes at least one ball screw nut driven by the screw shaft.

3. A scanner as in claim 1 where the driving means includes a drive motor integrated into the gauging head means and meshing with a linear belt fixed in a cross direction in the beam for driving the gauging head means.

4. A scanner as in claim 1 where the guide means includes a pair of rails and the gauging head means includes spaced electromagnets for interacting with the rails to provide a linear motor for driving the gauging head.

5. A scanner as in claim 3 where the drive motor includes a rotary encoder.

6. A scanner as in claim 3 where the gauging head includes sonic linear transducer means for indicating position by use of a tensioned metal band clamped in the beam in a CD.

7. A scanner for measuring at least one parameter of a sheet of material moving in a machine direction(MD) including gauging head means mounted for cross direction (CD) movement across the sheet, and perpendicular to the MD, from one edge of the sheet to the other comprising:
- at least one tubular beam suspended over or under the sheet in the CD from one the edge to the other, the beam having a continuous slot in the CD in proximity to such sheet to allow the gauging means to measure the parameter;
- guide means inside the tubular beam on which the gauging head means is interiorly mounted for CD movement within the tubular beam, such gauging head means having a face exposed through the slot to the sheet without physical interference for measuring a parameter of the sheet;
- seal belt means substantially contained within the tubular beam and connected to the gauging head for sealing the length of the slot in the CD to protect the interior of the beam and the gauging head from ambient dust, dirt, and air, the sealing belt means including an opening at the gauging head to allow direct communication, without interference, between the gauging head face and the moving sheet said seal belt means being clamped;
- and journalled shaft means in the beam for driving the gauging head means in the CD.

8. A scanner as in claim 7 where the opening in the seal belt means is provided by a portion of the belt means looping around the interior portion of the gauging head carried by a plurality of rollers.

9. A scanner as in claim 8 where one of the rollers is flexibly biased to provide tensioning for the seal belt means.

10. A scanner for measuring at least one parameter of a sheet of material moving in a machine direction(MD) including gauging head means mounted for cross direction (CD) movement across the sheet, and perpendicular to the MD, from one edge of the sheet to the other comprising:
- at least one tubular beam suspended over or under the sheet in the CD from one the edge to the other, the beam having a continuous slot in the CD in proximity to such sheet to allow the gauging means to measure the parameter;
- guide means inside the tubular beam on which the gauging head means is interiorly mounted for CD movement within the tubular beam, such gauging head means having a face exposed through the slot to the sheet without physical interference for measuring a parameter of the sheet said guide means including at least one rail on which said gauging head is movable;
- seal belt means substantially contained within the tubular beam and forming a loop within said beam connected to the gauging head for sealing the length of the slot in the CD to protect the interior of the beam and the gauging head from ambient dust, dirt, and air, the sealing belt means including an opening at the gauging head to allow direct communication, without interference, between the gauging head face and the moving sheet;
- and motor means for driving said loop and the gauging head in the CD.

11. A scanner as in claim 10 where the guide means includes a pair of rails and the gauging head means including spaced electromagnets for interacting with the rails to form magnetic levitation bearings.

12. A scanner as in claim 10 where the guide means includes a pair of rails and the gauging head means includes bearing block means for riding on the rails and having air outlets to provide air bearings.

13. A scanner as in claim 10 where the guide means includes a pair of rails, one of the rails being flat and the other cantilevered from a side wall of the beam and the gauging head means including opposed rollers for gliding on the rails the cantilevered rail providing positioning.

14. A scanner as in claim 10 where the guide means includes a single faceted rail on which the gauging head means is cantilevered for CD movement.

15. A scanner as in claim 10 where the gauging head means includes mirror means for reflecting infrared parameter information to a receiver mounted at an end of the beam.

16. A scanner as in claim 10 where the gauging head means includes a flexible fiber optic cable for transmitting infrared parameter information to a receiver mounted at the end of the beam.

17. A scanner for measuring at least one parameter of a sheet of material moving in a machine direction(MD) including gauging head means mounted for cross direction (CD) movement across the sheet, and perpendicular to the MD, from one edge of the sheet to the other comprising:
- at least one tubular beam suspended over or under the sheet in the CD from one the edge to the other, the beam having a continuous slot in the CD in proximity to such sheet to allow the gauging means to measure the parameter;
- guide means inside the tubular beam on which the gauging head means is interiorly mounted for CD movement within the tubular beam, such gauging head means having a face exposed through the slot to the sheet without physical interference for measuring a parameter of the sheet;
- seal belt means substantially contained within the tubular beam for sealing the length of the slot in the CD to protect the interior of the beam and the gauging head from ambient dust, dirt, and air, the sealing belt means including an opening at the gauging head to allow direct communication, without interference, between the gauging head face and the moving sheet said seal belt means being fixed along the entire length of the slot and is formed by a pair of flexible seal strips the gauging head means including two pairs of rollers for spreading the strips to provide the opening;
- and means for driving the gauging head means in the CD.

* * * * *